United States Patent
Skrzynska et al.

(10) Patent No.: US 9,550,715 B2
(45) Date of Patent: Jan. 24, 2017

(54) METHOD FOR SYNTHESISING GLYCOLIC ACID

(71) Applicants: Elzbieta Skrzynska, Cracow (PL); Franck Dumeignil, Villeneuve d'Ascq (FR); Mickaël Capron, Bachy (FR); Louise Duhamel, Villeneuve d'Ascq (FR)

(72) Inventors: Elzbieta Skrzynska, Cracow (PL); Franck Dumeignil, Villeneuve d'Ascq (FR); Mickaël Capron, Bachy (FR); Louise Duhamel, Villeneuve d'Ascq (FR)

(73) Assignees: PIVERT, Venette (FR); CENTRE NATIONAL DE LA RECHERCHE SCIENTIFIQUE (CNRS), Paris (FR); UNIVERSITÉ DES SCIENCES ET TECHNOLOGIES DE LILLE 1, Villeneuve d'Ascq (FR)

( * ) Notice: Subject to any disclaimer, the term of this patent is extended or adjusted under 35 U.S.C. 154(b) by 0 days.

(21) Appl. No.: 14/896,969

(22) PCT Filed: May 26, 2014

(86) PCT No.: PCT/IB2014/061725
§ 371 (c)(1),
(2) Date: Dec. 9, 2015

(87) PCT Pub. No.: WO2014/199256
PCT Pub. Date: Dec. 18, 2014

(65) Prior Publication Data
US 2016/0130209 A1     May 12, 2016

(30) Foreign Application Priority Data
Jun. 10, 2013 (FR) ...................................... 1355321

(51) Int. Cl.
*C07C 51/235* (2006.01)
*B01J 37/03* (2006.01)
*B01J 23/50* (2006.01)
*C07C 51/23* (2006.01)

(52) U.S. Cl.
CPC .............. *C07C 51/235* (2013.01); *B01J 23/50* (2013.01); *B01J 37/035* (2013.01); *C07C 51/23* (2013.01)

(58) Field of Classification Search
CPC ......... C07C 51/235; C07C 51/23; B01J 23/50; B01J 37/035
See application file for complete search history.

(56) References Cited

U.S. PATENT DOCUMENTS

| | | | |
|---|---|---|---|
| 4,548,921 A | 10/1985 | Geus et al. | |
| 5,274,187 A | 12/1993 | Kimura et al. | |

FOREIGN PATENT DOCUMENTS

| | | |
|---|---|---|
| CN | 1775351 A | 5/2006 |
| CN | 101279911 A | 10/2008 |
| CN | 101284774 A | 10/2008 |
| EP | 0091165 A1 | 10/1983 |
| FR | 2424264 A1 | 11/1979 |
| JP | S59112838 A | 6/1984 |

OTHER PUBLICATIONS

Hirasawa et al, Catalysis Science & Technology, 2012, 2(6), 1150-52.*
Hirasawa et al, J of Catalysis, 2013, 300, 205-216.*
Gosselin, Daniel, "International Search Report," prepared for PCT/IB2014/061725, as mailed Aug. 11, 2014, four pages.
Ketchie, et al.; "Influence of Gold Particle Size on the Aqueous-Phase Oxidation of Carbon Monoxide and Glycerol"; Journal of Catalysis, vol. 250, No. 1; Jun. 29, 2007; pp. 94-101.

* cited by examiner

*Primary Examiner* — Shailendra Kumar
(74) *Attorney, Agent, or Firm* — Winstead PC

(57) ABSTRACT

The invention relates to a method for synthesizing glycolic acid or one of the salts thereof, including the following step: placing glycerol and an oxidizing agent in contact with one another in a reaction medium in the presence of a silver-based catalyst on a substrate, said substrate including a material selected from the group consisting of $CeO_2$, basic $Al_2O_3$ optionally doped with a calcium or cerium oxide, an amphoteric resin, $ZrO_2$, and a mixture of said materials. The invention also relates to the use of a silver-based catalyst on a substrate that can be used in said method.

10 Claims, 2 Drawing Sheets

METHOD FOR SYNTHESISING GLYCOLIC ACID

This application is a 371 of PCT/IB2014/061725, filed on May 26, 2014.

FIELD OF THE INVENTION

The present invention relates to a process which makes possible the oxidation of glycerol to give glycolic acid by the catalytic route. The present invention also relates to a silver-based catalyst and to the use of a silver-based catalyst for the synthesis of glycolic acid from glycerol.

CONTEXT OF THE INVENTION

Glycolic acid of formula $CH_2(OH)COOH$, also known as hydroxyacetic acid, is used as monomer in the preparation of polyglycolic acid and also in the preparation of other biocompatible copolymers, such as polylactides-co-glycolide (PLGA) copolymers. Mention may be made, among other uses of glycolic acid, of its use in the textile industry as drying and dyeing agent. Glycolic acid can also participate in the composition of certain ready-made meals as preservative or taste enhancer. Glycolic acid is often introduced into polymer emulsions, into solvents and into additives for inks in order to improve the gloss and the fluidity thereof. It is also used in cosmetics, by virtue of its excellent ability to penetrate the skin, generally in facial scrubs. It can reduce wrinkles, acne or hyperpigmentation.

At the industrial level, glycolic acid is synthesized from compounds of fossil origin and is generally prepared by reaction between chloroacetic acid and sodium hydroxide according to the following reaction: $ClCH_2CO_2H + NaOH \rightarrow HOCH_2CO_2H + NaCl$.

Nowadays, other alternative routes, not operated industrially, are known, such as the carbonylation reaction between formaldehyde and synthesis gas ($CO+H_2$). The use can also be envisaged of a synthesis via the hydrogenation of oxalic acid. Glycolic acid can also be prepared by the enzymatic route.

Studies presented in the literature show that a high selectivity for glycolic acid is not observed for the catalysts commonly used, such as catalysts based on gold, platinum or palladium. Generally, the major product resulting from the reaction, catalyzed or noncatalyzed, for the oxidation of glycerol is glyceric acid ($CH_2(OH)CH(OH)COOH$).

Furthermore, the syntheses of glycolic acid presented in the literature are carried out in the presence of bases (for example NaOH). The base is generally used in large excess, with a [base]/[glycerol] ratio of the order of 4. This amount of added base results in the production of large amounts of salts during the acidification necessary for the recovery of the target molecules. These amounts increase not only the production costs but also the environmental impact of the synthesis.

DESCRIPTION OF THE INVENTION

It is an aim of the present invention thus to overcome one or more of these disadvantages, in particular by providing an alternative to the use of resources of fossil origin for the production of glycolic acid, by the use of biobased glycerol.

Another aim of the invention is to obtain the synthesis of glycolic acid from glycerol with a good selectivity and/or a good conversion value.

Finally, the invention also relates to a novel type of catalyst based on silver on a support for the synthesis of organic compounds.

According to a first embodiment, the invention relates to the use of a catalyst based on silver on a support in the synthesis of glycolic acid from glycerol. Thus, a subject matter of the invention is in particular a process for the synthesis of glycolic acid or of one of its salts comprising the following step:

bringing glycerol and an oxidizing agent into contact in a reaction medium in the presence of a catalyst based on silver on a support.

Preferably, said support comprises a material chosen from the group consisting of $CeO_2$, basic $Al_2O_3$, optionally doped with calcium or cerium, an amphoteric resin, $ZrO_2$ and a mixture of these materials.

The term "catalyst based on silver on a support" denotes compounds comprising silver in the metal form deposited on one (or more) other material(s) acting as support. Preferably, the catalyst comprises only silver as metal entity or is the main component of the catalyst. Preferably, the catalyst on a support does not comprise other noble metals (in particular, platinum and gold and possibly rhodium, osmium, palladium, ruthenium and iridium) or comprises a low amount thereof. The term "low amount" is understood to mean not more than 5% of the total amount of metal (for example Ag), preferably not more than 2.5% and more preferably still not more than 1%.

According to a preferred embodiment, it is advantageous for a base which produces hydroxide ions, such as sodium hydroxide or potassium hydroxide, ammonia or their mixtures to be present in the reaction medium. The introduction of a base makes it possible in particular to maintain a high pH. The pH of the reaction medium is preferably greater than or equal to 8, advantageously greater than or equal to 9, for example greater than or equal to 10.

Thus, according to this preferred embodiment of the invention, the molar ratio of the hydroxide ions to the glycerol [OH]/[gly] brought together can be approximately 4 or at least 4.

However, according to another embodiment of the invention, which is also preferred, this ratio of the molar concentration of hydroxide ions present in the reaction mixture to the glycerol [OH]/[gly] is less than or equal to 3 and preferably less than or equal to 2. More particularly, the process according to the invention can advantageously be carried out in the presence of a concentration of base, the [OH]/[gly] ratio of which is less than or equal to 1.5, more particularly less than or equal to 1.2 and advantageously less than or equal to 1. The [OH]/[gly] ratio is nevertheless advantageously greater than 0.4, so as to make possible sufficient degrees of conversion, for example of greater than 5. This ratio is advantageously chosen to be equal to 1±0.2. This is because, beyond the ratio of 1, the degree of conversion of the glycerol has a tendency to stagnate and not to increase substantially up to a ratio of approximately 4. Thus, surprisingly, a ratio of approximately 1 is substantially as effective as a ratio of 2 in terms of degree of conversion of glycerol or in terms of selectivity for glycolic acid.

This low amount of base brings about a decrease in the amount of the salts produced during a possible subsequent step of neutralization of the reaction medium which may be carried out for the recovery of the reaction products and more particularly of the glycolic acid. This neutralization can be carried out by virtue of one or more acids and in particular an inorganic acid, such as sulfuric acid. The amount of acid used is generally chosen in order to neutralize the reaction medium, that is to say that it is chosen so as to obtain an amount of hydronium ion equivalent to the amount of base introduced in the preceding step.

The glycerol used in the process according to the invention can be pure, in aqueous solution and/or as a mixture with other compounds. The glycerol can advantageously be of vegetable origin (biobased); for example, it can originate from rapeseed oil or sunflower oil.

The oxidizing agent used is preferably oxygen, either directly in the form of molecular oxygen $O_2$ or in another form such as hydrogen peroxide $H_2O_2$. Molecular oxygen can be used, pure or as a mixture (such as air), under pressure (for example from 1 to 10 bar, preferably approximately 5 bar) or at atmospheric pressure.

Preferably, the reaction medium is an aqueous medium, comprising more than 50%, advantageously more than 80%, by weight of water.

The reaction temperature can be chosen within a range from 50 to 150° C. Preferably, it is chosen within a range from 55 to 110° C., advantageously from 60 to 105° C., for example 100° C.

The reaction is advantageously carried out with continuous stirring, for example by applying a rotation of 1500 to 2000 rpm to the mixture.

The catalyst based on silver on a support is a catalyst, the proportion of the weight of Ag with respect to the weight of the support of which can vary from 10 to 0.2% (for example, 5±0.5%), more particularly from 5 to 0.5% Ag/support and in particular from 1 to 2% Ag/support. A ratio of approximately 1.5±0.1% is particularly advantageous. This catalyst can comprise another metal but a catalyst essentially comprising only silver as metal entity (that is to say, nonoxidized) is preferred in order to carry out the invention. According to a preferred embodiment of the invention, the catalyst comprises, as metal entity, only silver and optionally dopants, these dopants being described below.

Preferably, the amount of catalyst used is chosen so that the glycerol/catalyst ratio by weight in the reaction medium is chosen within a range extending from 2 to 100, preferably from 5 to 20, more particularly from 5 to 15.

The support of the catalyst is preferably chosen from the group consisting of not strongly acidic resins, metal oxides and their mixtures. For example, the support can be alumina or an amphoteric resin.

Particularly preferably, the support comprises an oxide chosen from the group consisting of basic alumina $Al_2O_3$, cerium oxide $CeO_2$, zirconium oxide $ZrO_2$ and a mixture of these oxides. The choice of such supports makes it possible to obtain a high degree of conversion and also a high selectivity, in particular which are greater than 40%.

The expression "basic alumina" denotes a material of formula $Al_2O_3$ exhibiting a Hammett acidity of between +7.8 and +8.9 (acidity measured respectively with cresol red and thymol blue). This same basicity can also be measured by pH-metry by adding, to an aqueous solution, 5 g of basic alumina in 95 g of water. For the basic aluminas used, the pH is greater than 9, whereas, under the some conditions, an alumina will exhibit a pH of between 6 and 8 and an acidic alumina will exhibit a pH of less than 6. A basic alumina makes it possible to obtain degrees of conversion of the glycerol which are much greater than those obtained using γ-alumina or acidic alumina. For example, the degree of conversion can be multiplied by 3, 5, indeed even 6, and can reach approximately 40%. Likewise, the selectivity of a catalyst according to the invention, the support of which is a basic alumina, can be improved by 5%, indeed even by 15%, with respect to the selectivity of a nonbasic alumina.

The not strongly acidic resins which can be used as support of the catalyst are generally synthetic polymers based on organic molecules. These resins are commonly based on styrenes crosslinked using different amounts of divinylbenzene in order to obtain polymers having different sizes and structures. Acrylic-based polymers can also be used. These resins are often provided in the form of beads.

These polymers, such as poly(styrene-divinylbenzene)s and polyacrylics, are generally functionalized by the presence of acid groups (for example sulfonic acid or carboxylic acid or their salts) or basic groups (for example quaternary ammonium ions or ammonium hydroxides). Some resins exhibit both acidic groups and basic groups and are known as amphoteric resins. Preferably, the resins used as support are chosen from the group consisting of basic resins and/or amphoteric resins. Resins of the latter type give particularly satisfactory results.

The term "not strongly acidic resins" is understood to mean resins exhibiting an acidity on the Hammett scale ($H_0$) or HA of greater than 2, preferably of greater than or equal to 6. Basic or amphoteric resins preferably exhibit an $H_0$ of greater than or equal to 6. Amphoteric resins with an $H_0$ equal to 7±0.8 give good results.

In order to determine the $H_0$, the Hammett method uses a series of color indicators. Approximately 0.1-0.2 g of a sample of the support tested is immersed in 5 ml of a mixture of anhydrous toluene and of cyclohexane (6:1 vol/vol). 2-3 drops of a 0.1% solution of an indicator (see below) in toluene are added to the suspension. This suspension is mixed and the color of the catalytic surface is observed. Observation is continued for 20 min with occasional mixing of the sample.

The indicators used can be chosen, for example, from the following compounds:

Crystal violet/methyl violet 10B: $H_0$=0.8. For lower values, namely $H_0$=0.8, the color is yellow around 0.8 green and for greater values, $H_0$>0.8, blue.

Bromothymol blue: $H_0$=7.2. The acidic color is yellow and the basic form is blue.

Phenol red: $H_0$=7.8. The acidic form is yellow and the basic form is red.

Thymol blue: $H_0$=8.9. The classic acidic form is yellow and the basic form is blue.

Indigo carmine: $H_0$=12.2. The acidic form is blue and the basic form is yellow.

Malachite green: $H_0$=13.0. The classic acidic form is blue-green and the basic form is colorless.

The metal oxide used as support can be chosen from the group consisting of aluminum, zinc, zirconium, lanthanum, magnesium, calcium, titanium and silicon oxides and their mixtures. Such a support can in particular comprise a modified oxide, such as basic alumina, doped with one or more other metal oxides (for example Bi, Sn, Co, Ni, Zn, La, Mo, Mn, Ce, W, Ca, and the like), bringing about a change in the acid-base properties of the oxide. Cerium, calcium, tungsten and molybdenum oxides are preferred dopants. The term "dopant" is understood to mean that the amounts used are low, for example less than 3 mmol of the atom used as dopant and preferably 1.5 mmol, with respect to 1 g of support. The doping of the support is carried out in the following way: the support is impregnated with a solution of the salt of the atom under consideration (for example, an ammonium or nitrate salt, for example $Ce(NO_3)_3$ or $Ca(NO_3)_2$) in the proportions described above and the powder obtained is subsequently dried (for example by heating at 110° C. for 24 h) and then calcined under air (for example at 550° C. for 3 h). Advantageously, this calcination is carried out by following a rise in temperature of approximately 10° C./min. The conditions exemplified above can obviously vary. A variation of approximately 25%, preferably 10%, can be envisaged as not significantly affecting the results. However, it is advisable to choose a calcination temperature which does not degrade the catalysts.

In particular, doping the support with cerium and/or calcium makes it possible to obtain greater degrees of conversion than those obtained with pure silver. Furthermore, doping with calcium makes it possible to achieve a greater selectivity for glycolic acid than that obtained with pure silver on the same support.

Oxides which are particularly preferred are basic alumina and oxides comprising amine functional groups (such as APTES (3-aminopropyl)triethoxysilane (CAS #919-30-2), APDEMS, APDMES and APTMS).

According to a preferred embodiment of the invention, the catalyst is a catalyst on a support of formula $Ag/CeO_2$, basic $Ag/Al_2O_3$, optionally doped with calcium oxide (CaO) or with cerium oxide ($CeO_2$), or Ag/IR45.

The process according to the invention makes it possible to obtain a good selectivity for glycolic acid. This selectivity is generally greater than or equal to 30%, it can be greater than 40% and it can even be greater than 50%.

This selectivity is advantageously combined with a degree of conversion exceeding 20%, for example of more than 35% and advantageously more than 40%.

The invention also relates to a product, such as glycolic acid, obtained directly by the process of synthesis described in the present patent application.

The invention also relates to a catalyst based on silver on a support and in particular an $Ag/Al_2O_3$ or Ag/amphoteric resin catalyst.

According to a specific embodiment, the catalyst according to the invention is obtained or is capable of being obtained by the process comprising the following steps:
a) dissolving a silver-based compound; and
b) bringing the silver-based compound and the support together, under mild conditions, in order to attach the silver to said support.

Preferably, the silver-based compound is a silver oxide, in particular silver nitrate.

Preferably, the solvent of the silver-based compound comprises an alcohol, such as methanol.

Preferably, the mixture is produced in the presence of an alcohol-based solvent, such as methanol. Said mixture is advantageously heated.

Preferably, step b) between the silver-based compound and the support comprises a step of reducing the silver oxide to give silver metal, which is then available to be attached to the support. This reduction step can be carried out by the addition of a reducing compound, such as formaldehyde or also hydrazine ($N_2H_4$) or sodium borohydride ($NaBH_4$). Optionally, this step is followed by a heating step.

Preferably, the attaching step comprises a step of neutralizing the solution. This step can be carried out by the addition of a base. The pH can then be adjusted by this addition to within a range extending approximately from 7 to 8.

Preferably, the support is one of the supports described above and in particular it can be chosen from the group consisting of resins and supports based on oxide comprising amine functional groups.

Preferably, the support used is dehydrated (dried) before it is suspended in the solvent of the reaction.

Thus, according to a preferred embodiment, a catalyst according to the invention is capable of being obtained by the following process of synthesis:

A support as described above, carefully dried before use, is immersed in methanol (V=100 ml per 10 g of support). Silver nitrate, dissolved in a water/methanol mixture, is slowly added dropwise to this suspension, mixed and heated (T≈64° C.), in order to obtain a charge of silver of approximately 1.5% by weight. Formaldehyde (formaldehyde/metals=10 molar) is then added in order to reduce the silver. The mixture thus obtained is mixed and heated (T≈64° C.) for 1 h. The pH of the mixture is subsequently adjusted to 7-8 with a sodium hydroxide solution. The mixture is then heated at the same temperature, with stirring, for an additional 20 minutes. The mixture is finally cooled to ambient temperature and filtered. The catalyst is subsequently washed with distilled water and dried at 110° C. for 24 h.

A catalyst according to the invention is, for example, an Ag/resin catalyst having a proportion of silver metal ranging from 1 to 2% and in particular of approximately 1.5%.

The invention thus relates to a catalyst as described in the present patent application and also to its process of manufacture and to its use as catalyst for the synthesis of glycerol or other organic compounds.

BRIEF DESCRIPTION OF THE DRAWINGS

A better understanding of the invention will be obtained on reading the appended figures, which are provided by way of examples and do not exhibit a limiting nature, in which.

DETAILED DESCRIPTION OF THE INVENTION

EXAMPLE 1

Figure 1:
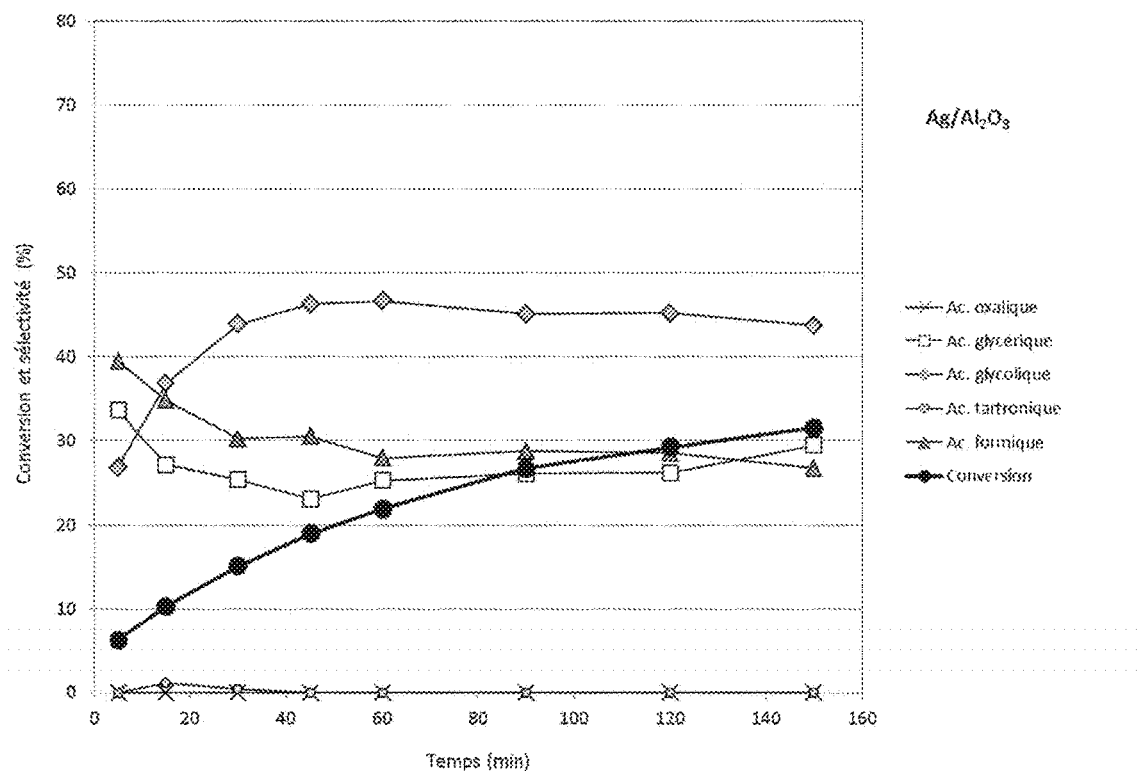
FIG. 1 represents the amount of products present during the reaction for the conversion of glycerol into different synthesis products described in example 3 as a function of the reaction time, this reaction taking place in the presence of a 1.486 wt % $Ag/Al_2O_3$ catalyst according to the invention and as described in example 1.

Synthesis of a Catalyst on Alumina According to the Invention: 1.46 wt % $Ag/Al_2O_3$ 9.9643 g of basic $Al_2O_3$ (Merck—BET~120 m²/g) and 75 ml of MeOH were heated with stirring at 67° C. for one hour.

After this period of time, 0.2332 g of $AgNO_3$ (eq. 0.1481 g of Ag), dissolved in 25 ml of MeOH, was slowly added to the reaction mixture. The beaker and the funnel were washed with an additional 30 ml of distilled water, which were also added to the reaction mixture.

Heating with stirring was continued for 1 h and then 26.4 ml (0.018 mol) of formaldehyde (HCHO) were added. Up to this stage, the color of the suspension is off white.

After 1 h, 13.2 ml of an NaOH solution (0.3M) were introduced into the solution, and the latter became dark brown, Heating under stirring is continued for 1.5 h.

After this period of time, the solution is slowly cooled down to ambient temperature and filtered. The filtrate obtained is washed with 50 ml of distilled water and then dried at 110° C. for 12 h. The color of the powder collected is dark grey.

The catalyst obtained is named according to the convention in force according to its nominal weight of charge, that is to say the nominal percentage by weight of silver used, with respect to the total weight of the catalyst.

EXAMPLE 2

Synthesis of a Catalyst on Resin According to the Invention: 1.486 Ag/IR45 (Calculated for the Dry Weight of the Resin)

The support chosen is IR45(OH), a resin formed of polystyrene polymers highly connected to one another and which are functionalized by amine groups, sold by Rohm & Haas. This resin is a neutral or amphoteric resin, $H_0=7.2$-7.8. 9.1485 g of IR45(OH) resin (6.7535 g by dry weight as 26.2% of the weight is lost during the initial drying) are dried and then added to 75 ml of MeOH: this mixture is subsequently heated with stirring at 67° C. for one hour.

After this period of time, 0.1581 g of $AgNO_3$ (eq. 0.1004 g of Ag), dissolved in 25 ml of MeOH, was slowly added to the reaction mixture. The beaker and the dropping funnel were washed with an additional 30 ml of distilled water, which were also added to the reaction mixture.

Heating under stirring was continued for one hour and then 0.012 mol of acid HCHO (9 ml of solution) was added. After one hour, 9 ml of NaOH solution (0.3M) were introduced into the solution. Heating under stirring was continued for 1.5 hours.

After this period, the solution was slowly cooled to ambient temperature and filtered. The filtrate is washed with 50 ml of distilled water and then dried at 110° C. for 12 h. The color of the powder collected is nonuniform and exhibits two colors: orange and green.

EXAMPLE 3

Use of the Catalyst of Example 1 in the Synthesis of Glycolic Acid from Glycerol The oxidation of glycerol in the liquid phase is carried out in a 300 ml stainless steel reactor equipped with a gas entrainment impeller, with four baffles, with a thermocouple and with a system for feeding with thermally regulated oxygen. 200 ml of an aqueous glycerol solution ([gly] =0.3M) are heated to the desired temperature of 60° C.

The sodium hydroxide (molar ratio NaOH/Gly=4) and the catalyst (ratio by weight gly/cat=11 (g/g)) are introduced into the reactor ($t_0$) and the system is pressurized with oxygen (5 bar) with continuous stirring (1500 rpm). The temperature and the $O_2$ partial pressure are continuously monitored while the sampling is carried out periodically. The products are analyzed by high performance liquid chromatography (HPLC) using a device of Agilent 1200 type equipped with a Rezex ROA-Organic Acid H+ column (300×7.8 mm) and with a refractive index detector (RID). A solution of $H_2SO_4$ (0.0025M) in demineralized water (0.5 ml·min$^{-1}$) is used as eluent. The identification and the quantification of the products obtained are carried out by comparison with the corresponding calibration curves.

The catalyst composed of approximately 1% of silver supported on alumina makes it possible to obtain a selectivity for glycolic acid (that is to say, the molar amount of glycolic acid formed with respect to the glycerol consumed), stable over the whole of the experiment, or approximately 50% (cf. FIG. 1). The two other products formed, in a similar amount, are glyceric acid and formic acid (each 25%). The degree of conversion is greater than 30%.

EXAMPLE 4

Use of the Catalyst of Example 2 in the Synthesis of Glycolic Acid from Glyercol The oxidation of glycerol in the liquid phase is carried out in a 300 ml stainless steel reactor equipped with a gas entrainment impeller, with four baffles, with a thermocouple and with a system for feeding with thermally regulated oxygen. 200 ml of an aqueous glycerol solution ([gly] =0.3M) are heated to the desired temperature of 100° C.

The sodium hydroxide (molar ratio NaOH/Gly=1) and the catalyst (ratio by weight gly/cat=5.5 (g/g)) are introduced into the reactor ($t_0$) and the system is pressurized with oxygen (5 bar) with continuous stirring (1500 rpm). The temperature and the $O_2$ partial pressure are continuously monitored while the sampling is carried out periodically. The products are analyzed with an Agilent 1200 HPLC device equipped with a Rezex ROA-Organic Acid H+ column (300×7.8 mm) and with a refractive index detector (RID). A solution of $H_2SO_4$ (0.0025M) in demineralized water (0.5 ml·min$^{-1}$) is used as eluent. The identification and the quantification of the products obtained are carried out by comparison with the corresponding calibration curves.

Figure 2:
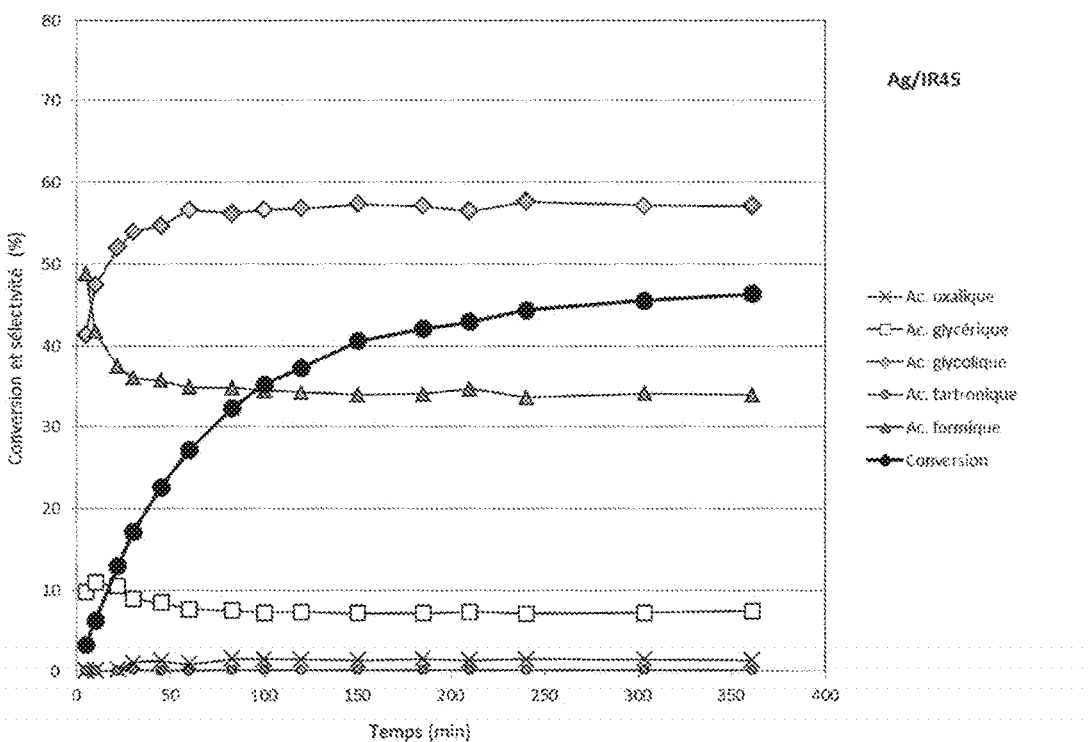
FIG. 2 represents the amount of products present during the reaction for the conversion of glycerol into different synthesis products described in example 4 as a function of the reaction time, this reaction taking place in the presence of a 1.486 wt % Ag/IR45 catalyst according to the invention and as described in example 4.

In this example, the use of a low amount of base (NaOH/Gly=1) makes it possible to obtain very good results after one hour of reaction (35% conversion and 55% selectivity for glycolic acid, cf. FIG. 2). The use of an amphoteric and/or neutral support is thus preferred.

The use of purely acidic resin (IRA120, HA=0.8) results in the conversion of the glycerol into glyceric acid. The use of a highly basic resin (IRA400, Fluka, HA>14) converts the glycerol into glyceric acid and into glycolic acid in the some proportions (selectivity=30%).

EXAMPLE 5

Figure 3:
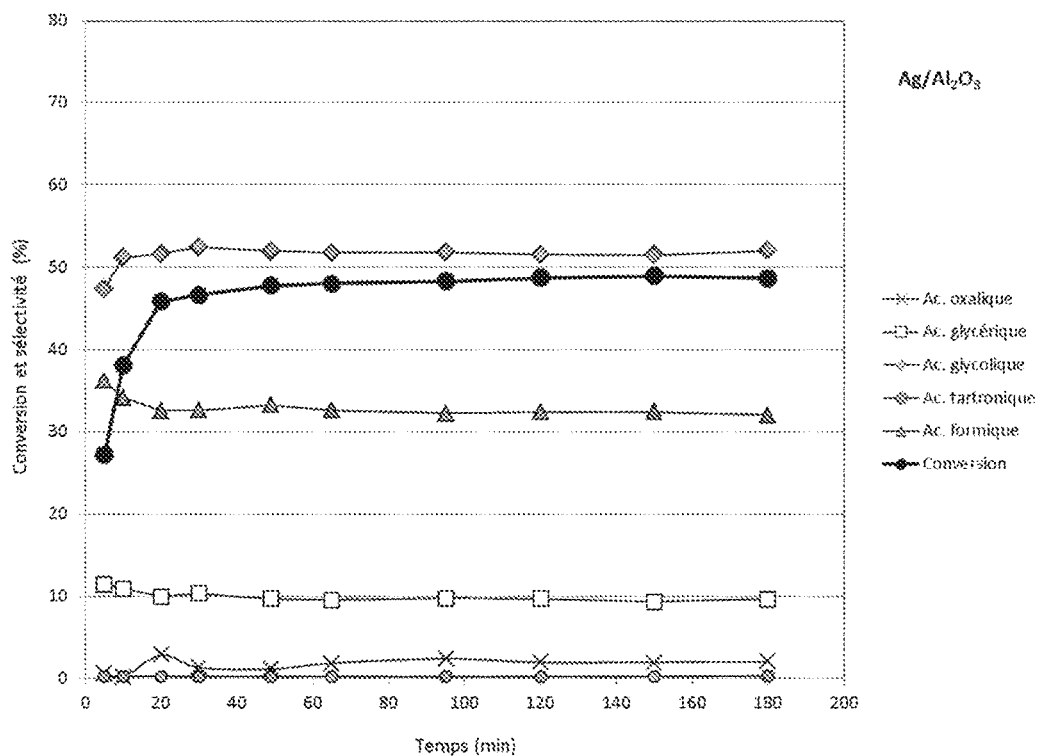
FIG. 3 represents the amount of products present during the reaction for the conversion of glycerol into different synthesis products of example 5.

Use of the Catalyst of Example 1 in the Synthesis of Glycolic Acid from Glycerol Using a Reduced Concentration of Base Example 4 was repeated with the catalyst of example 1 (1.486 wt % Ag/$Al_2O_3$) and the results obtained, presented in FIG. 3, are similar to those of example 4.

EXAMPLE 6

Method for the Synthesis of Glycolic Acid Using a Catalyst of Silver on a $CeO_2$ Support Preparation of the $CeO_2$ Support An aqueous cerium nitrate solution (0.5M) was prepared from cerium(III) nitrate hexahydrate (puriss p.a., ≥99.0%, Fluka). The solution obtained was added dropwise to a solution (in excess) of triethylamine (1.5M) diluted in methanol. The hydroxide precipitate obtained was recovered by filtration. It was subsequently washed and rinsed with water and methanol several times. It was dried in an oven at 100° C. The solid was subsequently ground into the form of a fine powder and then calcined under air at 500° C. for 4 h.

The synthesis of the catalyst was carried out according to the procedure of example 1. The synthesis of glycolic acid was carried out according to the procedure of example 3, that is to say at 60° C., 5 bar of $O_2$, 0.5 g of catalyst, 1500 rpm, 200 ml of a pure glycerol solution (0.3M) and a molar ratio NaOH/glycerol=4.

Figure 4:
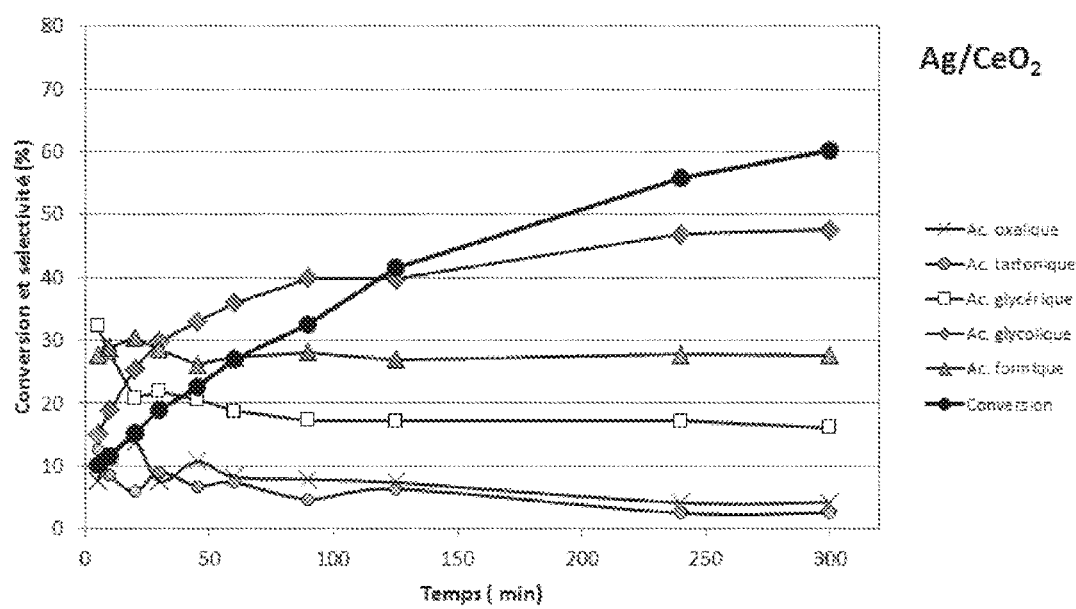
FIG. 4 represents the amount of products present during the reaction for the conversion of glycerol into different synthesis products of example 6.

This catalyst makes it possible to obtain a selectivity for glycolic acid (that is to say, the molar amount of glycolic acid formed with respect to the glycerol consumed), stable over the whole of the experiment, of approximately 50% (cf. FIG. 4). The degree of conversion is greater and approximately 60%.

The invention is not limited to the embodiments presented and other embodiments will be clearly apparent to a person skilled in the art.

The invention claimed is:

1. A process for the synthesis of glycolic acid or one of its salts comprising the following step:
    bringing glycerol and an oxidizing agent into contact in a reaction medium in the presence of a catalyst based on silver on a support, said support comprising a material chosen from the group consisting of $CeO_2$, basic $Al_2O_3$, optionally doped with a calcium or cerium oxide, an amphoteric resin, $ZrO_2$ and a mixture of these materials;
    wherein a base which produces hydroxide ions is present in the reaction medium; and
    wherein the molar ratio of hydroxide ions to glycerol [OH]/[gly] brought together is from 0.5 to 1.2.

2. The process as claimed in claim 1, wherein said catalyst is a catalyst on a support of formula $Ag/CeO_2$, basic $Ag/Al_2O_3$, optionally doped with calcium oxide or with cerium oxide, or Ag/IR45.

3. The process as claimed in claim 1, wherein the catalyst comprises, as metal entity, only silver.

4. The process as claimed in claim 1, wherein the pH of the reaction medium is greater than or equal to 8.

5. The process as claimed in claim 1, wherein which said oxidizing agent is oxygen.

6. The process as claimed in claim 1, wherein which the temperature of the reaction medium is chosen within a range extending from 50 to 150° C.

7. The process as claimed in claim 1, wherein the catalyst based on silver on a support is a catalyst, the proportion by weight of silver with respect to the support of which varies from 10 to 0.2%.

8. The process as claimed in claim 1, wherein the glycerol/catalyst ratio by weight in the reaction medium is chosen within a range extending from 2 to 100.

9. The process as claimed in claim 1, wherein the glycerol is of vegetable origin.

10. The process as claimed in claim 1, wherein the amounts of calcium or cerium oxides optionally used are less than 3 mmol of the atom used with respect to 1 g of support.

* * * * *